(12) United States Patent
Andre et al.

(10) Patent No.: US 8,039,028 B2
(45) Date of Patent: Oct. 18, 2011

(54) **USE OF AN EXTRACT OF THE ORCHID *VANDA COERULEA* AS A SKIN HYDRATING AGENT**

(76) Inventors: Patrice Andre, Neuville Aux Bois (FR); Jean-Christophe Archambault, Meung S/Loire (FR); Isabelle Renimel, Trainou (FR)

( * ) Notice: Subject to any disclaimer, the term of this patent is extended or adjusted under 35 U.S.C. 154(b) by 21 days.

(21) Appl. No.: 12/396,554

(22) Filed: Mar. 3, 2009

(65) Prior Publication Data

US 2009/0238848 A1  Sep. 24, 2009

(30) Foreign Application Priority Data

Mar. 3, 2008 (FR) ...................................... 0851382

(51) Int. Cl.
*A61K 36/00* (2006.01)

(52) U.S. Cl. ...................................................... 424/779

(58) Field of Classification Search .................. None
See application file for complete search history.

(56) References Cited

U.S. PATENT DOCUMENTS

2006/0165644 A1  7/2006  Tanaka

FOREIGN PATENT DOCUMENTS

| GB | 2381195 A * | 4/2003 |
| JP | 2006-257056 | 9/2006 |
| WO | WO2006-000689 | 1/2006 |

OTHER PUBLICATIONS

"Clarins Face Treatment Oil Blue Orchid" at (www.dooyoo.co.uk/clarins/face-treatment-oil-blue-orchid/1030259).*
L'huile Orchidee Bleu Clarins, XP002504778, Nov. 29, 2007.
Clarins Creme aux plantes Orchidee bleue, XP002504779, Jan. 12, 2002.
Plant Collections: Vanda Coerulea, XP002504800, Nov. 19, 2008.
Manandhar et al.; "An Ethnobotanical Survey of Herbal Drugs of Kaski District, Nepal"; Fitoterapia, 65(1):7-13, 1994.
Sigh et al.; "Traditional Phytotherapy of Some Medicinal Plants Used by the Tharus of the Nainital District, Uttar Pradesh, India"; Int. J. Pharmacogn.; 32(1):51-58, 1994.
Chawla et al.; "Chemical Studies and Antiinflammatory Activity of Vanda Roxburghii Roots"; Ind. J. Pharm. Sci, 54 (4):159-161, 1992.
Bulpitt; "The Uses and Misuses of Orchids in Medicine"; QJM, 98(9):625-631, 2005.
Sougrat et al.; "Functional Expression of AQP3 in Human Epidermis and Keratinocyte Cell Cultures"; Molecular Biology of the Cell; (9):499a, 1998.

* cited by examiner

*Primary Examiner* — Christopher R Tate
*Assistant Examiner* — Deborah A. Davis
(74) *Attorney, Agent, or Firm* — Furman Gregory Deptula; Wayne A. Keown

(57) ABSTRACT

The present invention relates to the use, in a cosmetic composition, of an extract of at least one part of an orchid of the species *Vanda coerulea*, as an agent for maintaining or restoring the hydration state of the skin, said composition also containing a cosmetically acceptable excipient.
This skin hydrating effect is obtained in particular by stimulating the expression of aquaporin 3 and of the LEKTI protein.
The invention also relates to a cosmetic skincare method for the purpose of improving the hydration state of said skin.

12 Claims, 2 Drawing Sheets

USE OF AN EXTRACT OF THE ORCHID *VANDA COERULEA* AS A SKIN HYDRATING AGENT

RELATED APPLICATIONS

This application claims priority to French Patent Application No. 0851382, filed on Mar. 3, 2008, the contents of which are incorporated herein by reference in its entirety.

TECHNICAL FIELD

The invention relates to a novel use of an extract of orchids of the species *Vanda coerulea* as a skin hydrating agent.

BACKGROUND

Orchids (Orchidaceae) are the subject of numerous research studies in the medicament or cosmetics field, aimed at identifying new compounds having advantageous properties. Orchids of the *Vanda* genus are epiphytic or epilithic orchids of the tropical forest of Asia and of Australia. They are monopodial orchids of low-altitude forests with a high atmospheric humidity. The genus comprises about fifty species with many hybrids. To date, research on plants of the *Vanda* genus is based on the knowledge and uses of these plants by local populations.

Manandhar et al. (Fitoterapia, 1994, 65 (1), 7-13) have described the use of *Vanda cristata* in the Kaski district of Nepal, for treating cuts and wounds using a paste based on the plant.

Sigh et al. have studied the traditional phytotherapy with medicinal plants used by the Tharu tribe of the Nainital district in the Uttar Pradesh region in India (Int. J. Pharmacogn., 1994 32 1, 51-58). These authors have described the use of a paste based on *Vanda tessallata* (synonym: *Vanda roxburghii*) obtained from the whole plant, and applied with salt to a bone fracture area. The publication also discloses the use of an aqueous extract of this same plant, administered orally for the same purpose.

Compositions intended for skin care, containing an extract of the plant *Vanda roxburghii*, have been described in Japanese Patent Application JP2006-257056, said extract being used in this composition as an oestrogenic agent for the treatment of skin aging.

Chawla et al. (Ind. J. Pharm. Sci., 1992, 54 (4), 159-61) have described the anti-inflammatory properties of an organic solvent-based extract obtained from *Vanda roxburghii* roots.

Bulpitt ("The uses and misuses of orchids in medicine", QJM, 2005, 98 (9), 625-31) indicates that the orchid *Vanda coerulea* appears to be part of the Indian pharmacopoeia.

Moreover, an extract of the whole plant of *Vanda coerulea*, sold under the name Biogreen Orchidée Bleue (Biogreen Blue Orchid) by Greentech SA, is also known. This extract is used as an antioxidant in cosmetic compositions.

Aquaporins or water channels are transmembrane protein systems that transport water and small molecules in solution, such as glycerol and urea, for example. The presence of type 3 aquaporins (AQP3) in the human epidermis, more specifically in the plasma membrane of the keratinocytes of human skin, and also the important role that these AQP-3s play in water transport within the human epidermis, are known (SOUGRAT et al., Molecular Biology of the Cell; November 1998; vol. 9, page 499a).

The LEKTI protein (lympho-epithelial Kazal type related inhibitor) is a protease inhibitor and is expressed in the granular layer of the epidermis located under the horny layer. Mutations in the SPINK5 gene, encoding this protein, result in a complete absence of the LEKTI protein in affected individuals, which leads to extreme disturbances of the cutaneous barrier, in particular at the level of the desmosomes.

Desmosomes enable mechanical attachment of the cells to one another, reinforcing the mechanical solidity of the sealing systems, and are binding sites for keratins between two cells (keratinocytes or corneocytes). They thus play an essential role in the cohesion between the cellular compartments which constitute the dermis and the epidermis and in the prevention of intercellular water evaporation, a phenomenon responsible for dryness of the skin.

In the absence of LEKTI production (in the case of patients suffering from Netherton's syndrome), a high degree of fragility of the skin is observed, resulting in severe dehydration.

It has been shown that the horny layer of the skin of knockout mice (which do not possess the SPINK5 gene) detaches from the rest of the epidermis due to degradation of the desmosomes, which bind the horny layer to the granular layer. This alteration is secondary to the hyperactivity of epidermal proteases which, in the absence of inhibition by LEKTI, degrade one of the key components of desmosomes, Desmoglein 1. LEKTI therefore plays a major role in regulating the process of desquamation of the epidermis by controlling the degradation of these attachment structures.

Stimulating AQP3 and of LEKTI may make it possible both to limit intercellular water evaporation and also to improve water transport within the epidermis. Thus there is a need for a simple, relatively inexpensive cosmetic agent capable of maintaining or reinforcing skin hydration.

SUMMARY OF THE INVENTION

The principal objective of the invention is to provide a novel cosmetic agent, capable of maintaining or reinforcing skin hydration. The present invention also relates to a cosmetic care method for hydrating the skin.

According to a first aspect, the invention relates to the use, in a cosmetic composition, of an extract of at least one part of an orchid of the species *Vanda coerulea*, as an agent for maintaining or restoring the hydration state of the skin, said composition also containing a cosmetically acceptable excipient.

According to a second aspect, the invention relates to a cosmetic skincare method for maintaining or restoring the hydration state of the skin, characterized in that it comprises the application, to the part of the skin of the face or of the body that is concerned, of an effective amount of an extract of an orchid of the species *Vanda coerulea* or of a composition which is the subject of the first aspect.

BRIEF DESCRIPTION OF THE FIGURES

FIG. 1 at D0
  FIG. 2 at D6
LEKTI:
FIG. 3 at D0
  FIG. 4 at D6

DETAILED DESCRIPTION OF THE PREFERRED EMBODIMENTS

Figure 1:
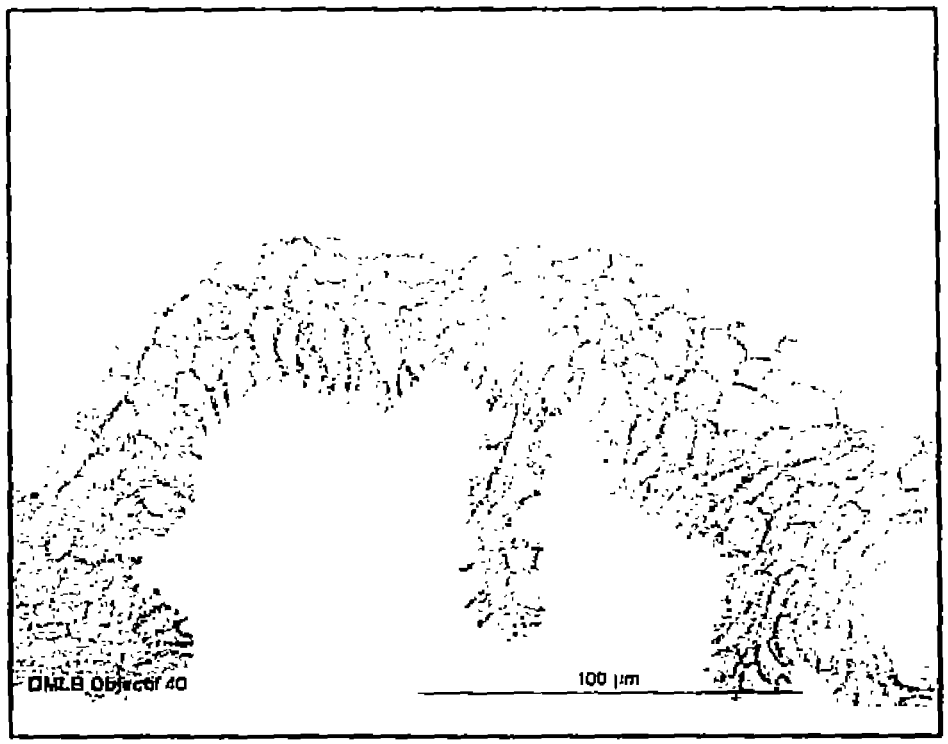
FIGS. 1 to 4 are given with reference to Example 2 and show histological sections observed by microscopy. They give the result of an immunolabelling of:
aquaporin 3.

It has now been discovered, completely unexpectedly by the inventors of the present invention that extracts of orchids of the species *Vanda coerulea* have new and remarkable skin hydrating properties which make their use particularly advantageous in cosmetic compositions for providing care where it is sought to maintain or to promote hydration of the skin.

In particular, these extracts of *Vanda coerulea* protect the skin against evaporation and provide a considerable hydrating effect by in particular improving water transport within the epidermis. It is this discovery which forms the basis of the present invention and explains the notable hydrating activities of the extracts of *Vanda coerulea*, which act simultaneously on two mechanisms responsible for correct hydration of the skin. In fact, the inventors have shown that the extract of *Vanda coerulea* increases the expression of two biological markers involved in the mechanisms of skin hydration, aquaporin 3 (AQP3) and the LEKTI protein (lympho-epithelial Kazal type related inhibitor).

The extract obtained from orchids of the species *Vanda coerulea* can thus be used as an active agent in a cosmetic composition comprising at least one cosmetically acceptable excipient, and intended to be applied to at least one part of the skin of the face or of the body, so as to obtain an effect of maintaining or reinforcing skin hydration.

The first subject of the present invention is thus the use, as a skin hydrating agent, of an extract obtained from a plant material formed from orchids of the species *Vanda coerulea*.

The plant material used may be the whole plant or a part of the plant, such as the leaves, the stem, the flowers or the roots.

The extract is preferably obtained from the stems and/or the roots and/or the leaves of the orchid, preferably the stems.

The extract is prepared by various extraction methods known to those skilled in the art.

However, the extraction is preferably carried out by bringing the selected plant material into contact with a polar solvent or a mixture of polar solvents.

Prior to this step of bringing at least one part of the plant into contact with at least one polar solvent, this plant part may be optionally dried and/or ground.

As polar solvent or mixture of polar solvents that can be used for the extraction step, a solvent or a mixture of solvents chosen from water, a $C_1$-$C_4$ alcohol, for example ethanol, and a $C_2$ to $C_6$ glycol preferably chosen from glycerol, butylene glycol and propylene glycol, and mixtures thereof, will advantageously be chosen.

According to one preferred embodiment of the invention, the extraction is carried out using an aqueous-alcoholic mixture, in particular a mixture of water and ethanol, preferably a mixture of water and ethanol comprising about 90% of water and 10% of ethanol, by volume.

According to another variant of the invention, the extraction may also be carried out by a process using a polar solvent in the subcritical state, said solvent being advantageously water in the subcritical state.

Prior to the extraction step itself, the plant material may have been dried and/or ground.

According to one preferred embodiment of the extraction, the plant material is in the dry and ground state.

The extraction may also optionally comprise at least one additional step constituted of a treatment of the extract aimed at partially or completely decolouring it, or in purifying it.

This decolouring step may, for example, comprise a treatment of the extract with a solution of a polar solvent or of a mixture of polar solvents, preferably a treatment with a solution of ethanol/water in a ratio of 70/30 v/v, in the presence of active carbon particles.

The decolouring may also comprise a treatment of the extract with an apolar solvent, for example a $C_6$-$C_7$ alkane, or alternatively with $CO_2$ in the supercritical state.

The extraction may be completed with a step of partial or complete elimination of the extraction solvents.

In the first case, the extract is generally concentrated until an aqueous concentrate devoid of significant amounts of organic solvents is obtained; in the second case, a dry residue is obtained.

Alternatively, the product of the extraction step may be lyophilized or atomized so as to be in the form of a powder.

The powder may be used as it is in a cosmetic or dermatological composition or may be redispersed in a solvent or a mixture of solvents.

In general, the product of the extraction step may be dissolved or dispersed in a solvent or a mixture of solvents, so as to used as an active agent in the cosmetic compositions covered according to the invention.

The solvent or the mixture of solvents in which the extract is dissolved or dispersed may be identical to or different from that having served for the extraction.

The extract may also be adsorbed onto a support advantageously chosen from porous or nonporous nylon powders, and micas, or any lamellar mineral substance.

In this case, the extract used is preferably an aqueous extract.

The cosmetic composition comprises an effective amount of extract for obtaining the desired effect.

The composition thus preferably comprises from 0.001% to 5%, preferably from 0.01% to 1%, by dry weight of extract.

The tests carried out by the inventors have shown that the properties of the extract can also be obtained or improved in cosmetic or dermatological compositions in which the extract is combined with other active agents having cosmetic effects similar and/or complementary to that of the extract of *Vanda coerulea*.

Thus, the extract can be combined with one or more molecules and/or one or more plant extracts having hydrating properties, such as glycols, in particular glycerol, or natural polyols, natural or synthetic ceramides, urea, hyaluronic acid, or else an extract of *Ajuga turkestanica*.

The extract may also be advantageously combined, in cosmetic compositions, with at least one extract of at least one other plant belonging to the orchid family (Orchidaceae). This additional extract of another plant belonging to the orchid family may in particular be an extract of at least one orchid of the *Vanda* genus.

The compositions covered by the invention may comprise, at the same time, an extract of at least one part of the *Vanda coerulea* plant combined with at least one extract of at least one part of another orchid of the *Vanda* genus as defined above, and, optionally, at least one other extract of another plant belonging to the orchid family.

In addition to the extract defined above, the cosmetic composition comprises at least one cosmetically or dermatologically acceptable excipient which can be chosen from pigments, dyes, polymers, surfactants, rheology agents, fragrances, electrolytes, pH modifiers, antioxidants and preservatives, and mixtures thereof.

The cosmetic composition may, for example, be a serum, a lotion, a cream or else a hydrogel, preferably a mask, or may be in the form of a stick, or else a patch.

The extracts and the compositions have an effect that is particularly desired for maintaining or reinforcing the hydration state of the skin, when said extract or said composition is applied to the skin of the face or of the body.

The present invention relates, as disclosed above, to the use of the extracts as defined above as a cosmetic agent for maintaining or reinforcing the hydration state of the skin.

As clearly emerges from the examples hereinafter, the applicant has demonstrated the advantage of the extracts of the plant *Vanda coerulea* for improving the activities listed below:

stimulation of AQP3 expression, stimulation of LEKTI protein expression.

A subject of the invention is also a cosmetic care method using the extract defined above or a cosmetic composition as defined above comprising an effective amount of said extract, for obtaining an effect of preventing or slowing down the appearance of the signs of dryness of the skin.

Said cosmetic care method comprises the application, to at least one area, of the skin of the face or of the body that is concerned, of a composition as described above and comprising an extract as defined above.

In the examples, all the percentages are given by weight, the temperature is in degrees Celsius, and the pressure is atmospheric pressure, unless otherwise indicated.

In addition to the extract of the species *Vanda coerulea*, the composition may comprise one or more other plant extracts, obtained from whole plants or from parts of plants.

These plants may be either orchids, in particular of the *Vanda* genus, or plants of another family, known to have properties similar or complementary to those demonstrated for orchids of the species *Vanda coerulea*.

Plants of which the extracts are known to slow down or prevent the appearance of the signs of dryness of the skin may in particular be chosen.

Other objectives, characteristics and advantages of the invention will become clearly apparent in the light of the explanatory description which follows, given with reference to examples of preparation of extracts and of tests demonstrating the properties of the extracts and to an example of a cosmetic composition using such extracts, given simply by way of illustration and which could not therefore in any way limit the scope of the invention.

EXAMPLES

Example 1

Preparation of an Extract of *Vanda coerulea* Stems a) Preparation of an Extract of Stems The plant material formed from *Vanda coerulea* stems, in the dry state, is ground extemporaneously.

10 g of ground plant material are introduced into a 250 ml round-bottomed flask, into which 150 ml of an ethanol/water mixture (90/10 v/v) are introduced.

The round-bottomed flask surmounted with a bulb condenser with magnetic stirring is heated in a thermostated bath, to the reflux of the solvent.

The reflux is maintained for 30 minutes with stirring.

Once the heating has been stopped, the round-bottomed flask is left to cool to ambient temperature outside the bath.

The mixture is then vacuum-filtered through a Büchner funnel with a Whatman 70 µm GF/F filter and a tared flask: filtrate 1 is obtained.

The cake is washed on the Büchner funnel with 50 ml of the extraction solvent: filtrate 2 is obtained.

The 2 filtrates are combined and weighed.

The filtrate thus obtained is introduced into a pre-tared round-bottomed flask, and then concentrated to dryness on a rotary evaporator in a bath of water placed at a maximum temperature of 50° C.

The dry residue thus obtained is quantified in order to determine the extraction yield by mass, expressed relatively to the mass of dry plant introduced.

The extraction yield (expressed as mass of dry extract obtained per 100 g of starting plant material in the dry ground state) is 8.9.

b) Preparation of an Extract of Roots

The procedure is carried out according to the same protocol in order to prepare an extract of *Vanda coerulea* roots (extract No. 2).

These two extracts will be used in the examples which follow, either separately or as a mixture, and combined in various proportions.

Example 2

Tests for Activity of Extracts of *Vanda coerulea*

The doses for using the extracts are predetermined by means of the XTT test (reagent: tetrazolium salt) on a cell culture of two cell lines, HaCaT cells (line of keratinocytes immortalized in vitro) and normal human fibroblasts (NHF).

Glossary of the Histological Terms Used

Spongiose: intercellular oedema without breaking of desmosome bonds.

Pycnotic nuclei: nuclei in a state of nuclear degeneration leading to cellular necrosis.

Cellular oedema: Swelling of the cell.

Parakeratosis: keratinization in the granular layer, the last living epidermal layer.

Materials and Methods

The dry extract obtained according to Example 1, from *Vanda coerulea* stems, is dissolved in DMSO at a concentration of 1.5% by weight of dry extract.

Preparation of Biopsies 15 explants with a diameter of approximately 10 mm are prepared from an abdominal plasty from a 40-year-old woman. They are kept alive in BEM specific medium (BIO-EC Explant Medium).

The explants are divided up into 2 batches of 6 explants plus 3 explants at T0, divided up in the following way:

6 explants for the control (formulation devoid of active agent), 6 explants having the same control formulation, but itself containing 5% by weight of the extract of *Vanda coerulea*, i.e. a final concentration of 0.075% by weight of dry extract.

The products are applied topically at a dose of 2 mg per explant and spread with a small spatula.

The applications are carried out at D0, D1, D2, D4, D6 and D8.

Samples and Histologies

Samples

Samples of the explants are taken for histology at times D0, D6 and D10.

Samples are taken from 3 explants of the T0 batch, at D0, and samples are taken from 3 explants of each batch at D6 and D10.

Each explant is immediately cut into two. One half is fixed in formol buffered at a pH of 7.5 with a phosphate buffer solution, and the other half is frozen at −80° C.

Histology

After fixing for 24 hours in the buffered formol, the samples are dehydrated and impregnated with paraffin using a Leica 1020 automated dehydration device. They are placed in blocks using a Leica EG 1160 coating station. 5 µm sections are cut on a Leica RM 2125 Minot microtome and stuck onto superfrost silanized histological glass slides.

The frozen samples are cut at 7 μm in a Leica CM 3050 cryostat. The sections are stuck onto silanized histological glass slides for immunolabelling.

The microscopic observations are carried out by optical microscopy, using a Leica type DMLB microscope, with the ×40 objective. The images are taken with a Sony DXC 390P 3CCD camera and stored using the Leica IM1000 data archiving software.

General Morphology

The general morphology is observed on sections embedded in a paraffin gel and stained with Masson trichrome, Goldner variant.

Immunolabelling

Aquaporin 3

The AQP3 is labelled with a polyclonal anti-AQP3 from Chemicon, ref AB 3276, on a rabbit. It is carried out with a Vectastain Universal Vector biotin/streptavidin amplifying system and revealed in 3,3-diaminobenzidine (DAB), a substrate molecule for peroxidase. The nuclei are counterstained with Masson's hemalun.

LEKTI

LEKTI is labelled with anti-LEKTI, a monoclonal antibody, clone 1C11G6, Santa Cruz ref SC-32330, on formol-fixed, paraffin-embedded sections, with a biotin/streptavidin amplifying system, and revealed with fluorescein isothiocyanate (FITC). The nuclei are counterstained with propidium iodide.

RESULTS

General Morphology

At D0:

On the Untreated Explants:

The stratum corneum is not very thick, is very slightly laminated, and is fully keratinized at the surface and at its base. The epidermis shows 4 to 5 cell strata with keratinocytes exhibiting good morphology. The outline of the dermal-epidermal junction is sharp. The papillary dermis shows quite thick collagen fibres forming a more or less dense network. It is well cellularized.

At D6:

On the Untreated Explants:

The stratum corneum is moderately thick, very moderately laminated and moderately keratinized at the surface. Parakeratosis is very moderate. The epidermis shows 4 to 5 cell strata with keratinocytes exhibiting good morphology. The outline of the dermal-epidermal junction is sharp. The papillary dermis shows quite thick collagen fibres forming a more or less dense network. It is well cellularized.

On the Explants Treated with the Formulation Containing the Extract of *Vanda coerulea*:

The stratum corneum is moderately thick, moderately laminated, and slightly keratinized at the surface. Parakeratosis is moderate. The epidermis shows 5 to 6 cell strata with keratinocytes exhibiting good morphology. Spongiosis is weak in the basal position of the epidermis. The outline of the dermal-epidermal junction is sharp. The papillary dermis shows thick collagen fibres forming a dense network. It is well cellularized.

At D10:

On the Untreated Explants:

The stratum corneum is quite thick, quite well laminated and moderately keratinized at the surface. Parakeratosis is weak. The epidermis shows 4 to 5 cell strata with keratinocytes exhibiting good morphology. The outline of the dermal-epidermal junction is very sharp. The papillary dermis shows quite thick collagen fibres forming a network that is not very dense. It is well cellularized.

On the Explants Treated with the Formulation Containing the Extract of *Vanda coerulea*:

The stratum corneum is quite thick, quite well laminated, and moderately keratinized at the surface. Parakeratosis is strong. The epidermis shows 5 to 6 cell strata with keratinocytes exhibiting a very average morphology. Many keratinocytes are slightly oedematous in the prickle cell layers, with cells containing pycnotic nuclei and perinuclear oedema in the upper prickle cell layers. The outline of the dermal-epidermal junction is sharp. The papillary dermis shows thick collagen fibres forming a dense network. It is well cellularized.

Aquaporin 3 Immunolabelling

No labelling is observed on the sections on which the primary or secondary antibody was replaced with PBS.

At D0:

On the Untreated Explants (see FIG. 1):

The labelling is sharp, regular, and clearly on the membrane and pericellular. It is sharp and regular in the upper epidermal layers, and is not observed in the final cell stratum. It is quite sharp laterally in the basal layer.

Figure 2:
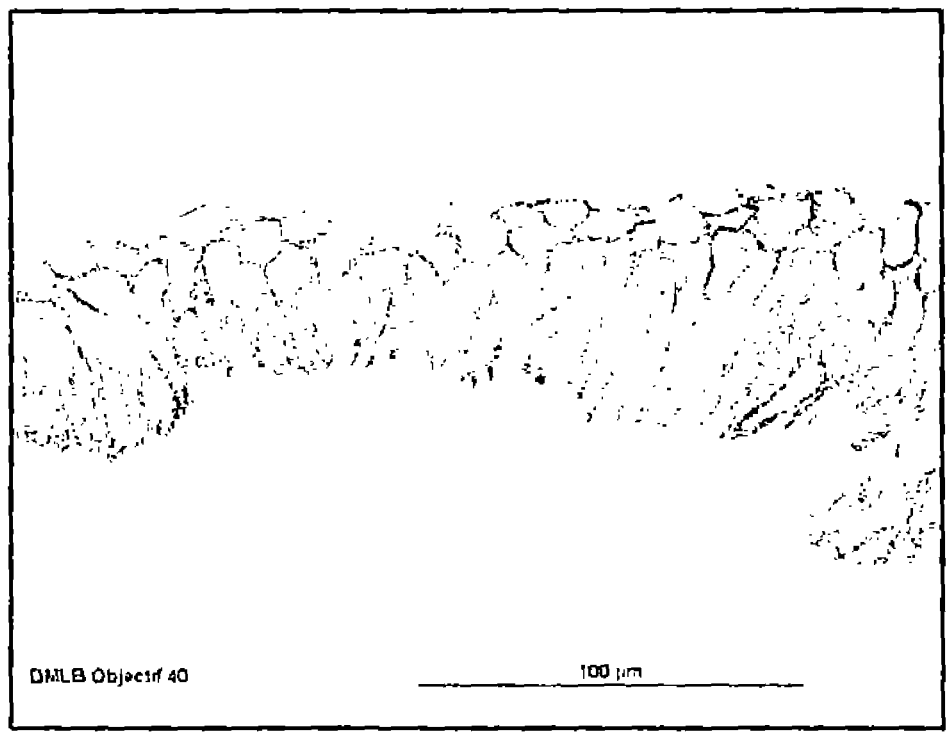

At D6:

On the Explants Treated with the Formulation Containing the Extract of *Vanda coerulea* (see FIG. 2):

The labelling is sharp, regular, and clearly on the membrane and pericellular. It is sharp and quite regular in the upper epidermal layers, and is not observed in the final cell stratum. It is very sharp all along the basal layer of the epidermis, at the dermal-epidermal junction, a sign of strong AQP3 expression activity in the deep layers of the epidermis.

LEKTI Immunolabelling:

No labelling is observed on the sections on which the primary or secondary antibody was replaced with PBS.

Figure 3:

At D0:

On the Untreated Explants (see FIG. 3):

The labelling is weak, quite regular, and on the membrane on 4 to 5 cell strata in the granular layer at the base of the stratum corneum. It is slightly observed on 2 to 3 cell strata in the stratum corneum. It is not observed in the underlying epidermal layers.

Figure 4:

At D6:

On the Explants Treated with the Formulation Containing the Extract of *Vanda coerulea* (see FIG. 4):

The labelling is quite sharp, quite regular, and clearly cytoplasmic on 2 to 3 cell strata in the granular layer at the base of the stratum corneum. It is hardly observed in the stratum corneum. It is slightly observed on 1 cell stratum in the underlying epidermal layers.

CONCLUSIONS

The extract of *Vanda coerulea* makes it possible to improve the regulation of epidermal desquamation processes, by controlling the degradation of these attachment structures by increasing the expression of LEKTI, which makes it possible to protect and reinforce the skin barrier, and thus the hydration of the skin.

Moreover, the extract has a particular efficacy for regulating water fluxes in the epidermis, through an effect on the regulation and/or the functionality of aquaporins AQP3, thus enabling better hydration of the basal layers of the epidermis.

Example 3

Cosmetic Composition Comprising the Extract of the Invention

The extract of orchids used as active agent in the following cosmetic composition is obtained by reproducing the method in Example 1.

The dry extract is dissolved at 1% w/w in a 60/40 v/v mixture of glycerol/water.

This solution is used as active agent for preparing the cosmetic composition below (% expressed as w/w):

| Phase A | |
|---|---|
| Solution containing 1% of extract of *Vanda coerulea* | 0.3% |
| Phenoxyethanol | 0.5% |
| Xanthan gum | 0.2% |
| Acrylates/C20-30 alkyl acrylate crosspolymers | 0.15% |
| Tetrasodium EDTA | 0.1% |
| Water | qs |

| Phase B | |
|---|---|
| Hydrogenated polyisobutene | 4% |
| Squalane | 3% |
| Caprylic/capric triglyceride | 3% |
| Pentylene glycol | 3% |
| Glyceryl stearate | 3% |
| PEG-100 stearate | 2.5% |
| Beeswax | 1.5% |
| Dicaprylyl carbonate | 1.5% |
| Cetyl alcohol | 1% |
| Stearyl alcohol | 1% |
| Dimethicone | 1% |

| Phase C | |
|---|---|
| Sodium hydroxide | 0.04% |
| Water | qs 100% |

The gelling agents of phase A are dispersed in water and then the mixture is heated at 80-85° C., before solubilizing all the other compounds, including the solution of extract of *Vanda coerulea*.

The compounds of phase B are heated at 85° C. so as to form a homogenous phase.

Phase A is emulsified in phase B using an Ystral mixer.

The oil/water emulsion thus obtained is finally neutralized with a 0.04% w/w aqueous sodium hydroxide solution, and then cooled.

The composition obtained is a moisturizing cream intended to be applied to the face or a part of the face.

What is claimed:

1. A method for maintaining or restoring the hydration state of the skin, comprising applying to a part of the skin of the face or of the body in need thereof, a cosmetic composition containing an effective amount of an extract of an orchid of the species *Vanda coerulea* for maintaining or restoring the hydration state of the skin, said composition also containing a cosmetically acceptable excipient.

2. The method according to claim 1, wherein said extract is an extract of an orchid part selected from the group consisting of the stem, the roots, the leaves, and mixtures thereof.

3. The method according to claim 1, wherein said extract is an extract of the stem.

4. The method according to claim 1, wherein said extract is obtained by bringing at least one part of said orchid, optionally dried, or ground, or both, into contact with at least one polar solvent.

5. The method according to claim 4, wherein said polar solvent is selected from the group consisting of water, $C_1$-$C_4$ alcohols, and $C_2$ to $C_6$ glycols, and mixtures thereof.

6. The method according to claim 5, wherein said solvent is an aqueous-ethanolic mixture.

7. The method according to claim 4, wherein said polar solvent is a solvent in the subcritical state.

8. The method according to claim 1, wherein said extract has been subjected to at least one decolouring, or purifying step, or both.

9. The method according to claim 1, wherein said composition also contains one or more molecules and/or one or more plant extracts having hydrating properties.

10. The method according to claim 1, wherein said composition is in the form of a serum, a lotion, a cream, a hydrogel, a mask, a stick or a patch.

11. The method according to claim 1, wherein the extract is a dry extract and wherein said composition contains from 0.001% to 5%, by weight, of the dry extract.

12. The method according to claim 1, wherein the extract is dry extract and wherein said composition contains from 0.01% to 1%, by weight, of the dry extract.

* * * * *